(12) United States Patent
Koch et al.

(10) Patent No.: US 10,726,512 B2
(45) Date of Patent: Jul. 28, 2020

(54) METHOD AND SYSTEM FOR INTEGRATION OF CLINICAL AND FACILITIES MANAGEMENT SYSTEMS

(71) Applicant: HDR Architecture, Inc., Omaha, NE (US)

(72) Inventors: Timothy E. Koch, Omaha, NE (US); Scott R. Winfrey, Omaha, NE (US); Von E. Lambert, White Heath, IL (US); Diane P. Rock, Wilmington, NC (US); Denise Bauer Nyberg, Cincinnati, OH (US); Thomas S. Hicks, Omaha, NE (US)

(73) Assignee: HDR Architecture, Inc., Omaha, NE (US)

( * ) Notice: Subject to any disclaimer, the term of this patent is extended or adjusted under 35 U.S.C. 154(b) by 0 days.

(21) Appl. No.: 16/422,358

(22) Filed: May 24, 2019

(65) Prior Publication Data
US 2019/0279324 A1    Sep. 12, 2019

Related U.S. Application Data

(63) Continuation of application No. 14/742,353, filed on Jun. 17, 2015, now Pat. No. 10,325,334, which is a
(Continued)

(51) Int. Cl.
*G16H 40/20* (2018.01)
*G06Q 50/22* (2018.01)
(Continued)

(52) U.S. Cl.
CPC .............. *G06Q 50/22* (2013.01); *G06Q 10/04* (2013.01); *G06Q 10/06* (2013.01); *G06Q 10/0631* (2013.01); *G16H 40/20* (2018.01)

(58) Field of Classification Search
CPC ........ G06Q 50/22; G06Q 10/04; G06Q 10/06; G06Q 10/0631; G06Q 10/06311;
(Continued)

(56) References Cited

U.S. PATENT DOCUMENTS 5,395,042 A    3/1995  Riley et al.
6,029,092 A    2/2000  Stein
(Continued)

OTHER PUBLICATIONS

ASHRAE Handbook (Year: 1999).*
(Continued)

*Primary Examiner* — Joseph D Burgess
(74) *Attorney, Agent, or Firm* — Erickson Kernell IP, LLC

(57) ABSTRACT

The present disclosure relates to an automated system for regulating the allocation of resources, or the dissemination of information within a healthcare facility. The automated system includes a context providing system capable of determining the state of a parameter and a facilities management system in communication with the context providing system. An integration protocol is configured to facilitate communication between the context providing system and the facilities management system and the facilities management system allocates resources or disseminates information based upon the value of the parameter provided by the context providing system.

12 Claims, 2 Drawing Sheets

Related U.S. Application Data continuation of application No. 12/941,197, filed on Nov. 8, 2010, now abandoned.

(60) Provisional application No. 61/259,313, filed on Nov. 9, 2009.

(51) Int. Cl.
*G06Q 10/04* (2012.01)
*G06Q 10/06* (2012.01)

(58) Field of Classification Search
CPC .. G06Q 10/06315; G06Q 50/24; G16H 40/20; G16H 40/60; G16H 40/67
See application file for complete search history.

(56) References Cited

U.S. PATENT DOCUMENTS

| | | | |
|---|---|---|---|
| 6,073,110 A * | 6/2000 | Rhodes | G06Q 10/06 705/7.12 |
| 6,968,295 B1 | 11/2005 | Carr | |
| 7,118,472 B2 | 10/2006 | Bjordal | |
| 7,392,661 B2 | 7/2008 | Alles | |
| 2002/0152298 A1 | 10/2002 | Kikta et al. | |
| 2004/0238653 A1 | 12/2004 | Alles | |
| 2005/0194455 A1 | 9/2005 | Alles | |
| 2007/0143451 A1 | 6/2007 | Huth et al. | |
| 2007/0239484 A1 | 10/2007 | Arond et al. | |
| 2008/0083234 A1 | 4/2008 | Krebs et al. | |
| 2008/0083834 A1 | 4/2008 | Krebs et al. | |
| 2008/0177423 A1 | 7/2008 | Brickfield et al. | |
| 2009/0125337 A1 | 5/2009 | Abri | |
| 2009/0302994 A1 * | 12/2009 | Rhee | H02J 13/0075 340/3.1 |
| 2010/0299517 A1 | 11/2010 | Jukic et al. | |
| 2017/0365024 A1 | 12/2017 | Koch | |

OTHER PUBLICATIONS

Tim Koch "Integration dreaming", Nov. 2007, Healthcare Design, vol. 7, No. 9, pp. 10, 12.
Johnson Controls Inc. "Operating Room Optimization" Oct. 29, 2013, http://www.johnsoncontrols.com/content/us/en/products/bu i ld ing_ efficiency/bu i ld ing/healthcare/energy-efficiency/optim izing-or. html.

* cited by examiner

METHOD AND SYSTEM FOR INTEGRATION OF CLINICAL AND FACILITIES MANAGEMENT SYSTEMS

CROSS-REFERENCE TO RELATED APPLICATIONS

This application is a continuation of co-pending U.S. patent application Ser. No. 14/742,353, filed on Jun. 17, 2015, which is a continuation of U.S. patent application Ser. No. 12/941,197, filed on Nov. 8, 2010, which claims priority to U.S. Provisional Patent Application Ser. No. 61/259,313 filed on Nov. 9, 2009, titled METHOD AND SYSTEM FOR INTEGRATION OF SCHEDULING AND BUILDING MANAGEMENT SYSTEMS each of which is incorporated by reference herein in its entirety.

BACKGROUND OF THE INVENTION

A variety of facilities employ context providing systems. Context providing systems are systems that include or have access to information that about the operation of the facility or its occupants. Healthcare facilities often include one or more context providing systems examples of which include, electronic record management systems, registration systems, and scheduling systems. These facilities can be quite large and require a substantial amount of energy or other resources when in operation. However, at any given time, only a portion of these facilities may be in use. This can result in substantial waste of energy and other resources.

One illustrative facility is a hospital having a surgical suite. Surgical suites have unique requirements for effective ventilation. For example, anesthetic gas and vapors that leak out into the surrounding room during medical and surgical procedures are considered waste anesthetic gases. They include nitrous oxide and halogenated agents (vapors) such as enflurane, isoflurane, sevoflurane, desflurane, and halothane. Potential adverse health effects of exposure to waste anesthetic gases include loss of consciousness, nausea, dizziness, headaches, fatigue, irritability, drowsiness, problems with coordination and judgment, as well as sterility, miscarriages, birth defects, cancer, and liver and kidney disease. Additionally, airborne contaminants such as microorganisms may contribute to post-operative infections in patients. These contaminants can most effectively be removed with adequate circulation that includes exchanges of the air in the operating room with clean filtered air.

To deal with the unique challenges of the surgical suite, the American Institute of Architects (AIA) suggests an air exchange rate of 15 air changes, with three outside air changes every hour. American Society of Heating, Refrigeration and Air Conditioning Engineers (ASHRAE) recommends 20-25 air changes per hour with 4-5 outside air changes per hour. It is common for systems to be designed to ASHRAE recommendations. Maintaining such high air exchange rates requires significantly more energy for a heating, ventilation, and air conditioning (HVAC) system than more typical HVAC applications. This makes operation of an HVAC system much more expensive for a surgical suite than it is for a comparable volume of commercial office space or other space.

One reason that specific environmental conditions are recommended is to reduce the risks associated with surgical site infections. In 2009, it was reported by the CDC that surgical site infections were the second most frequently reported nosocomial infection accounting for 22% (approximately 500,000 SSIs out of 27 million surgical procedures performed annually) of the 1.7 million nosocomial infections each year. Of the 1.7 million patients with nosocomial infections, 99,000 deaths resulted among hospitalized patients in the United States. For patients with surgical site infections that die, 77% of those patients' cause of death is from the surgical site infection. Depending on the location of the surgical site infection, it is estimated that healthcare costs can increase to upwards of $20-50,000, resulting in $1-10 billion dollars in healthcare costs for surgical site infections alone per year in the United States. Patients with surgical site infections had their hospital length of stay increase by 7.3 days.

Although it is not specifically known whether or not substandard operating room ventilation has a direct effect on the development of a surgical site infection without performing baseline testing on the care environment specifically, it would be to the advantage of the clinical personnel to be made aware of substandard air ventilation and support of the patient care environment so they can address any issues that may contribute to the decrease of patient safety where hospital acquired infections or more specifically perioperative surgical site infections are concerned. If it is possible to reduce surgical site infections with early notification of poor patient care environment air quality, naturally, not only would this affect contribute to a decreased length of stay and subsequent reduction in dollars spent on patient care to treat the surgical site infection, but also a more optimum patient experience.

Existing systems can provide for both an "occupied" mode and a "setback" mode for an HVAC system in use with an operating room. Typically such systems require direct intervention such as a manual input by a user. These systems allow for the case where a user may neglect to change the HVAC control mode for an operating room to occupied in advance of a surgical procedure. This results in wasted time as a room is brought to the correct operating conditions. Also, a user may neglect to setback the system after a surgical procedure is complete. This results in the operating room being maintained in an "occupied" mode for prolonged periods of time and accruing unnecessary utility costs associated with conditioning changing the air. Continuous communication between facility staff and clinical staff is not feasible in order to optimally set setback time schedule. For this reason, the use of time schedules are abandoned or set extremely conservatively. Another option that has been implemented is the use of occupancy sensors. These have had very limited effectiveness due to the frequency that staff enters the room at times other than for a surgical procedure. Such times are for cleaning, stocking supplies, moving equipment, and preparation.

Accordingly, there is a need for a method to allow automated control and monitoring of building systems based on inputs from a context providing system. There is also a need for a system and method that will reduce the total cost of HVAC operation for surgical suites. There is a further need for an HVAC and building control system that can automatically adjust the operating mode of a room based upon the actual use of the space.

SUMMARY OF THE INVENTION

One non-limiting embodiment of the present disclosure relates to an automated system for regulating the allocation of resources, or the dissemination of information within a healthcare facility. The automated system includes a context providing system capable of determining the state of a parameter and a facilities management system in communication with the context providing system. An integration protocol is configured to facilitate communication between the context providing system and the facilities management system and the facilities management system allocates resources or disseminates information based upon the value of the parameter provided by the context providing system.

Another aspect of the present disclosure relates to an automatic system for controlling an HVAC system for an area within a healthcare facility. The system includes a building management system and a clinical system. The clinical system may include schedule data relating to a usage schedule for the area. An integration protocol is configured to provide the schedule data to the building management system, whereby the building management system Yet another aspect of the present disclosure is a system for controlling an HVAC system in a building configured to regulate environmental conditions in a zone. The system includes a building control system configured to provide a control signal to the HVAC system and a scheduling system in communication with the building control system and including schedule of use data for the zone. The control signal provided is based upon the schedule of use data that is provided to the building control system by the scheduling system.

DETAILED DESCRIPTION

Reference will now be made to illustrative embodiments for use in healthcare facilities. Particular attention is provided to the facilitation of communication between a context providing system and a facilities management system where the context providing system is a surgical scheduling system and the facilities management system controls the HVAC system used to control the environment in a surgical suite. While this is a particularly important aspect of the present disclosure, it is by no means the exclusive one. The principles and concepts described will be applicable to other embodiments as discussed herein.

Figure 1:
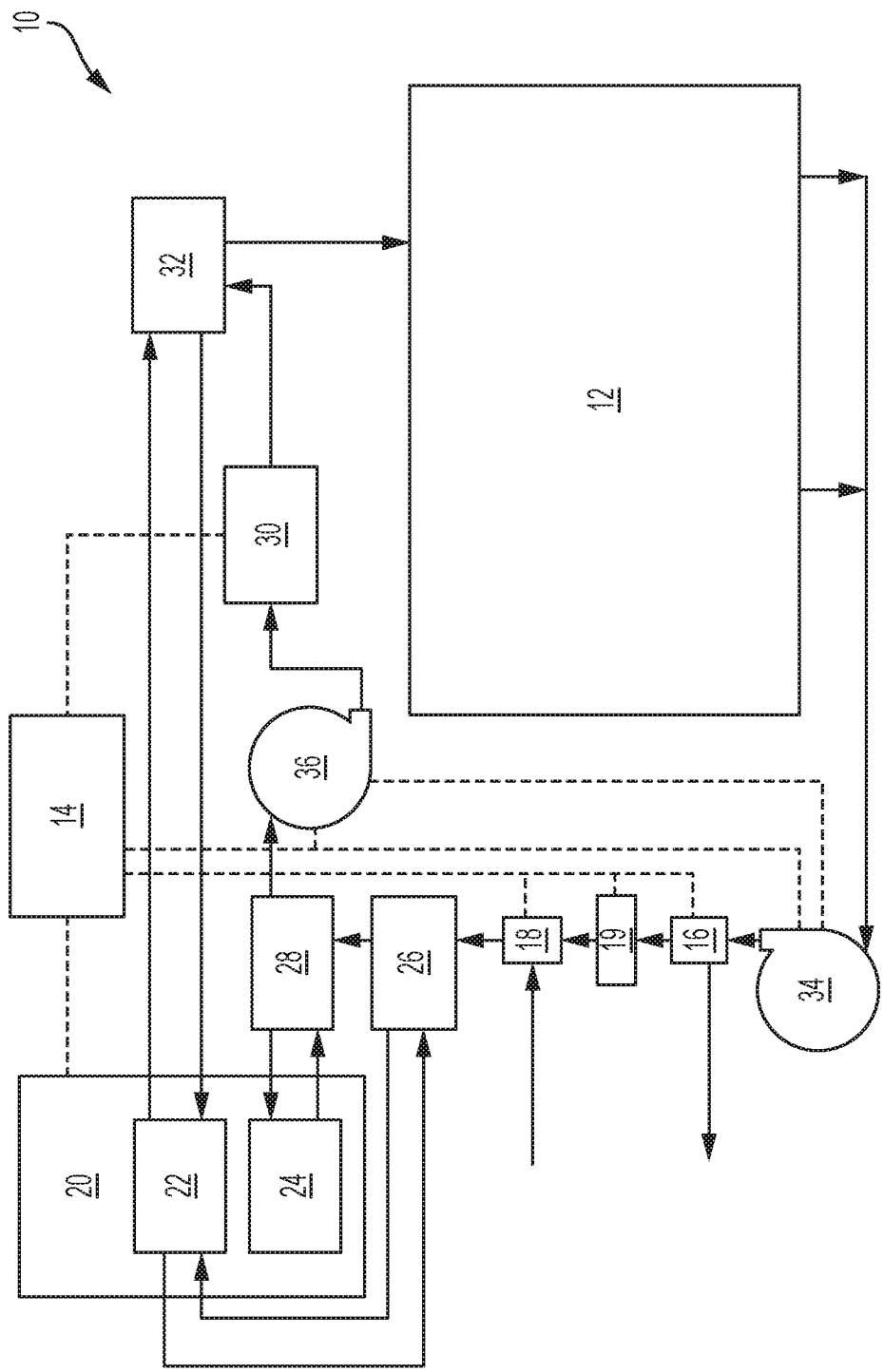
FIG. 1 is a schematic view of a prior art HVAC system for use with a surgical suite.

Referring to FIG. 1, a prior art HVAC system 10 for use in controlling the climate of a surgical suite or operating room 12 is provided to ventilate and heat or cool the suite. The HVAC system utilizes a building management system 14. For purposes of this description, the terms "building management system," "building automation system," building management and control system," or other similar terms may be considered interchangeable and refer to systems for controlling environmental and lighting conditions. Air is circulated out of the suite and mixed with outside air. Damper 16 allows for a portion of the air from operating room 12 to be vented as exhaust while outside air is drawn in through damper 18. The mixed air is then heated or cooled by heat exchangers/coils coupled to a central utility plant 20. The central utility plant 20 typically includes a boiler 22 for providing hot water or steam and a chiller 24 for providing chilled water to the heat exchangers/coils 26 and 28. Boiler 22 may also provide steam for humidification. The air is then passed through filter 30 to remove particulates. Filter 30 may be monitored by the building management system 14 to record loadings and provide an indication when the filter should be cleaned or replaced. The filtered air may then be passed through a reheat heat exchange 32 to that the air is supplied to the surgical suite at a temperature chosen to raise or lower the ambient temperature of the surgical suite to a preselected temperature. Blowers 34 and 36 are used to draw the return air out of the surgical suite and to drive the supply air in. Dampers and airflow measuring stations may be used to achieve a predetermined ratio of outside air to recirculated air. For example, the system may be configured to provide 15 air changes with three outside air changes every hour. In some embodiments, the system may be configured to provide 25 air changes per hour, or any other level of air circulation that may be delivered by the HVAC equipment.

The building management system is used to actively control the HVAC system of FIG. 1. Sensors detecting airflow, temperature, and/or humidity may be used by the building management system to determine settings for control dampers, control valves, and blowers to achieve the required temperature, humidity, and/or ventilation in the surgical suite. For example, temperature sensors in the surgical suite may be used to provide temperature readings used by a feedback loop to achieve or maintain a desired preset temperature in the surgical suite. The building management system may determine a set point based on an operating mode. The mode may be selected by a person wanting to change the operating mode.

Figure 2:
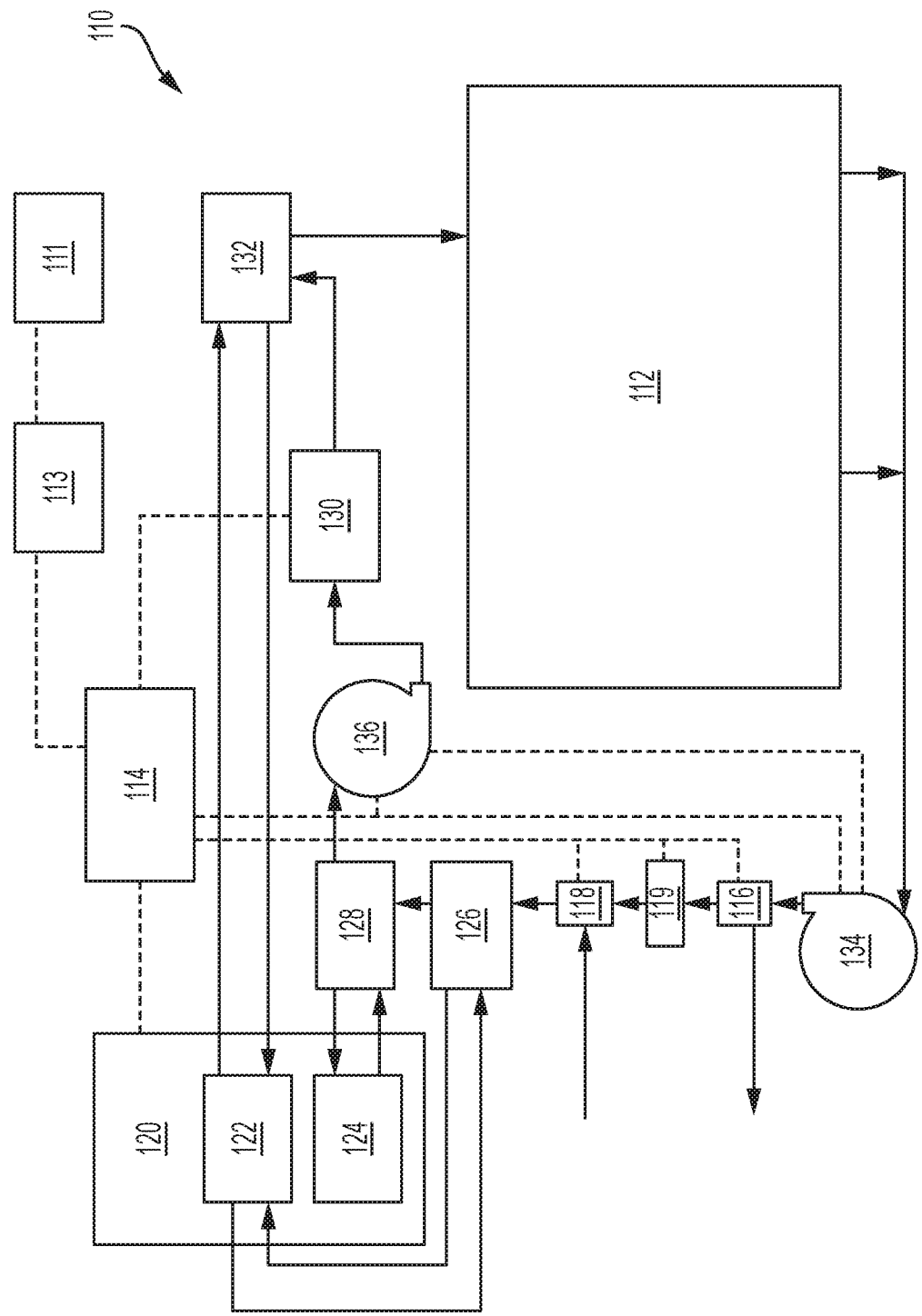
FIG. 2 is a schematic view for an improved HVAC system.

Referring to FIG. 2, a clinical system, shown as surgical suite scheduling system 111 is used to schedule surgical procedures throughout a facility. An integration protocol 113 is provided to translate and route scheduling data from the surgical scheduling system 111 to the building management system 114. One example of a suitable integration engine is CLOVERLEAF, an integration system provided by HEALTHVISION of Irving, Tex. For example, the integration engine translates data from the surgical scheduling system 111 that may be formatted in HEALTH LEVEL 7 (HL7) standard format, to a format such as XML. A second conversion may them be made from XML to a building management system compatible format (i.e., LONWORKS, BACNET, Modbus, etc.) that may be read by the building management system 114. The particulars of the integrations protocol, the number of conversion steps, formats and/or languages used should not be considered limiting to the scope of this disclosure. Rather, reference to such systems is made to illustrate some possible implementations of a communication link between a context providing system and a building management system in a healthcare facility.

Similarly to the system of FIG. 1, air is circulated out of the suite and mixed with outside air. Damper 116 allows for a portion of the air from operating room 112 to be vented as exhaust while outside air is drawn in through damper 118. Additionally, damper 116 may be placed inline with dampers 116 and 118 to further regulate the flow of air. The mixed air is then heated or cooled by heat exchangers/coils coupled to a central utility plant 120. The central utility plant 120 typically includes a boiler 122 for providing hot water or steam and a chiller 124 for providing chilled water to the heat exchangers/coils 126 and 128. Boiler 122 may also provide steam for humidification. The air is then passed through filter 130 to remove particulates. Filter 130 may be monitored by the building management system 114 to record loadings and provide an indication when the filter should be cleaned or replaced. In some embodiments, a particle counter may be placed in or in fluid communication with the air stream down stream of the filter. Such a device could be used to monitor actual performance of the filter and better indicate cleaning and/or replacement. The filtered air may then be passed through a reheat heat exchange 132 to that the air is supplied to the surgical suite at a temperature chosen to raise or lower the ambient temperature of the surgical suite to a preselected temperature. Blowers 134 and 136 are used to draw the return air out of the surgical suite and to drive the supply air in. Dampers and airflow measuring stations may be used to achieve a predetermined ratio of outside air to recirculated air. For example, the system may be configured to provide 15 air changes with three outside air changes every hour.

Another advantage that may be realized is in surgical suite scheduling for Level I trauma centers. These centers are required to keep a minimum of one operating room available and ready for a trauma patient at all times. Keeping a single room in this state can lead to substantial costs. Accordingly, the scheduling system may be integrated with the building management system in a way that allows one operating room to be available at all times, but it may not be a single room. Rather an efficient scheduling decision may be programmed by which one of several rooms is designated based on surgical and maintenance schedules for the other rooms.

FIG. 2 illustrates an air handling unit serving a single surgery room. This same concept can be applied to an air handling unit serving multiple surgery rooms. If this is done, supply and return air terminal units with air flow sensors would need to be provided for each surgery room. Other configurations may be possible; however, any such configuration preferably has the ability to keep the surgical suite positively pressurized at all times regardless of varying supply airflow. For example, in lieu of a return air terminal unit, a pressure monitor with return control damper may be used.

Information about surgical suite scheduling may then be used by the building management system 114 to determine which of two HVAC system modes should be used at a given time. In the present embodiment, when the system is in "Surgery" mode the HVAC system 110 operates to achieve a minimum of 15 air changes with three outside air changes every hour. This mode would by selected by the building management system 114 in advance of and during any scheduled surgical procedures. During downtimes when the surgical suite is not in use, the system may operate in a "Setback" mode. In Setback mode, the HVAC system 110 may operate to achieve 3.75 air changes per hour with 0.75 outside air changes. The AIA and ASHRAE state that the air changes can be reduced to 25% of suggested values during set back periods. Alternatively, other reduced levels of ventilation may be selected.

As an example, in a 600 square foot surgical suite with 10 foot ceilings, 6,000 cubic feet of air must be moved for each air change. Fifteen air changes per hour would require a flow rate of 90,000 cubic feet per hour or 1,500 cubic feet per minute. Additional energy is required to condition the three outside air changes that would represent 22,500 cubic feet per hour. In the Setback mode, 22,500 cubic feet per hour would be moved, with 4,500 cubic feet per hour of outside air. This significantly reduces the energy needed for blower and chiller equipment compared to the Surgery mode.

While it would be possible for hospital personnel to manually adjust the HVAC settings for a surgical suite based on a usage schedule, such methods are problematic. For example, failing to return the room to Setback mode after a surgical procedures results in wasted energy expenses. Failing to set the system to Surgery mode prior to a surgical procedure results in delays and downtime costs that can exceed the energy costs. The result has been that HVAC systems for surgical suites are operated at a high throughput nearly all the time. Occupancy sensors, which are also problematic, are unable to distinguish between surgery use and nonsurgery occupancy, such as cleaning. The computerized method of the present invention avoids such potential problems while reducing energy costs.

More than one set of operating conditions may be associated with the surgical mode. For example, different surgeons may have different preferred temperatures for the rooms in which they operate. To accommodate these different preferences, the surgical scheduling system could include a field for an identifier of the surgeon who will be operating in a room when it is scheduled to be in use. A database could be created that includes, among other things, the temperature preference for various surgeons. When the scheduling system communicates with the building management system to designate a room as "in use" a set point for the ambient temperature could also be provided from based on the scheduled surgeon's preference.

The operating conditions may also be varied based on the type of procedure scheduled. For example, some procedures may have a lower risk of secondary infection than other, more invasive procedures. In such cases, the number or air changes, temperature, humidity and/or other conditions may be set at level consistent with the procedure scheduled.

While the system has been described and is seen as most applicable to surgical suites, other applications may similarly exist. For example, the patient room HVAC settings can be adjusted based upon whether or not a patient is checked into a hospital, as such information is contained within a clinical system, such as the patient registration system. The same concept can apply to scheduled appointments for procedures such as radiology, endoscopy, colonoscopy, chemotherapy, dialysis, etc.

In general, the invention relates to the integration of context providing system (i.e. a healthcare clinical system) and a facility management system (i.e. a building control system that is used to control resource allocation and/or disseminate information about the facility). In an exemplary embodiment, the context providing system is the "master" and the facilities management system is "slaved" to it. The context providing system provides a parameter (i.e. "room in use," "type of procedure scheduled," etc.) to the facilities management system. The facilities management system then regulates climate control through a building management system, lighting, or other systems based on the parameter provided. As discussed herein, a facilities management system may include, as subsystems, lighting control systems, and building management systems (or building automation systems) configured to control environmental conditions. In some embodiments, the building management system may give feedback to the context providing system, or a third system (such as a reporting module), regarding the status of the system being controlled. This allows for an efficient allocation of resources throughout the facility at the times those resources are needed. Cost savings can then be realized in reduced staffing needs for facility personnel, or lower energy costs.

In some embodiments, the building management system or another system may be provided with a reporting module. The reporting module may be used to maintain a record of the conditions in the area being regulated. The data may include airflows, temperatures, relative humidity, or any other relevant parameter to be controlled. The record may be used retrospectively to evaluate the performance of the building management and HVAC systems, or it may be used to immediately determine if a measured parameter is outside of defined acceptable limits. For example, a notification may be provided immediately to the clinical and/or building staff should the airflow fall below a threshold level. This would allow for the immediate reaction by the staff to resolve the issue, or move the patient to an area that is in compliance with the set environmental conditions.

Accordingly, based on the description above, it has been shown that the integration of a surgical scheduling system with a building management system can be used to reduce HVAC system loadings and thereby reduce energy costs. Further, when coupled with a reporting module, the systems described herein can be used to potentially improve patient outcomes, and provide detailed records of system performance. Such records may be cross-referenced with patient data in a clinical system to determine the environmental conditions under which a particular procedure was performed.

While the benefits of providing communication between a context providing system and a building management system in a healthcare facility have been discussed in the context of controlling an HVAC system based on a surgical schedule system, it will be apparent to one of skill in the art that a healthcare facility can benefit in multiple other ways once a line of communication has been provided between the two systems. The following discussion of additional embodiments in which communication between a context providing system and a building management system can provide benefits in a healthcare facility. These embodiments are provided as examples and should not be considered limiting in nature.

In some embodiments, a surgical scheduling system may be in communication with a building management system to control an HVAC system as described herein. In addition, the set points for various parameters, such as temperature, air flow, and/or humidity, may be determined by a clinician preference that is stored in the surgical scheduling system based on which clinician will be working in the area. Additionally or alternatively, a set point may be determined based on the type of procedure scheduled to take place in the area. For example, a lower air flow or different temperature may be set for less invasive procedures.

In some such embodiments, the system may be configured for continuous commissioning. The building management system may be provided with environmental set points from the clinical system. The building management system will then provide continuous monitoring of those conditions, regulate the HVAC system to reach and/or maintain them, and notify facility and/or clinical staff in the event that one or more of the conditions is out of compliance based on data from the clinical system.

In some embodiments, a surgical scheduling system may be in communication with a building management system to control an HVAC system. Automatic reports may be periodically generated to record the temperature, air flow, humidity, particulate count, filter pressure drop, motor current draw, or other environmental factors that may be of clinical or facility interest. The data may be archived in a searchable database so that it may be referenced at a later time. Also, the data may be continuously compared to set points and tolerance ranges such that error reports may be automatically generated and shared with the appropriate building and/or clinical staff to indicate that a parameter is out of compliance based on data from the clinical system.

In addition to documenting instances in which a parameter is out of compliance, the system may also provide the facility and/or clinical staff with notifications and request feedback from the staff documenting when and how the issue was resolved.

In some embodiments, a patient information or registration system may be in communication with a building management system to control and HVAC system related to a zone of control. The zone may be an inpatient room which the patient information system will indicate as being occupied or vacant. The system may then provide set points for the HVAC system based on the occupancy status of the room. Alternatively, an occupied room may be associated with one or more set points (such as temperature) that are based on the patient's preference determined at the point of registration.

In some embodiments, a clinical system may be in communication with a building management system to control an HVAC system associated with a zone. The system may extract a set point for a parameter, such as temperature, associated with some time in the future, such as the scheduled start of a surgical procedure. The system then determines when to cycle on the HVAC system to reach the set point at the appropriate time. Additionally, the system may be provided with the ability to calculate if the controlled parameter will be in compliance by the scheduled time. If that is not the case, the system may inform the facility and/or clinical staff prior to the scheduled time so that the procedure may be rescheduled or moved to another room.

In some embodiments, the system may be configured to extract data about a patient in the patient information system for use in controlling the HVAC system. For example, the patient registration system may include a data field to indicate if the patient has a latex allergy. For patients with such allergies, the system could automatically set the HVAC system to reach the set point for air changes an hour earlier to reduce the presence of latex in the air.

In another embodiment in which the system extracts patient information, the building management system may vary HVAC operation based on the isolation status of a patient. For example, if a patient is to be isolated, the system may automatically be operated at full ventilation of a period before and after the isolated patient is to be in the zone (such as a surgical suite, inpatient room, radiology suite, or other testing area).

In general, the context providing system may be any clinical system (surgical or other clinical scheduler, patient information system, patient registration system, etc.) that includes patient data relevant to the way in which the building management system may most efficiently and safely operate. The context may include indications that a room is to be occupied or vacant, whether the patient has an allergy such as a latex allergy, whether the patient should be isolated, a preferred set point for an environmental condition either by a patient or clinician, a preferred set point for an environmental condition based on the type of procedure scheduled for the HVAC zone controlled by the building management system, or any other information relevant to efficient and safe building control.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that relative terms are intended to encompass different orientations of the device in addition to the orientation depicted in the Figures.

Moreover, it will be understood that although the terms first and second are used herein to describe various features, elements, regions, layers and/or sections, these features, elements, regions, layers and/or sections should not be limited by these terms. These terms are only used to distinguish one feature, element, region, layer or section from another feature, element, region, layer or section. Thus, a first feature, element, region, layer or section discussed below could be termed a second feature, element, region, layer or section, and similarly, a second without departing from the teachings of the present invention.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Further, as used herein the term "plurality" refers to at least two elements. Additionally, like numbers refer to like elements throughout. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required."

Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims.

The invention claimed is:

1. A system for integration of clinical and facilities management systems, comprising:
   a surgical suite scheduling system storing desired HVAC modes of operation for a surgical suite within a facility based on one or more parameters;
   a facilities management system comprising one or more heat exchangers, one or more dampers, and one or more blowers that provide recirculated air, outside air, heated air, chilled air, and combinations thereof to the facility and to the surgical suite; and
   an integration protocol that facilitates communication between the surgical suite scheduling system and the facilities management system; wherein the facilities management system receives requests for desired surgical suite HVAC conditions from the surgical suite scheduling system and commands at least one of the one or more dampers and/or one or more blowers to direct air through at least one of the one or more heat exchangers to provide desired heating, cooling, and air exchange conditions.

2. The system of claim 1, wherein the facilities management system controls the one or more heat exchangers, one or more dampers, and one or more blowers to provide a minimum of 15 air changes with 3 outside air changes every hour when the mode of operation is in surgery mode; and
   wherein the facilities management system controls the one or more heat exchangers, one or more dampers, and one or more blowers to provide 3.75 air changes with 0.75 outside air changes every hour when the mode of operation is in setback mode.

3. The system of claim 1, wherein the one or more parameters associated with the surgical suite comprise a desired temperature, a desired humidity level, a scheduled surgery, a scheduled surgeon, and combinations thereof.

4. The system of claim 3, wherein each of the scheduled surgery and scheduled surgeon parameters comprise a desired temperature, a desired humidity level, and combinations thereof.

5. The system of claim 1, wherein the facilities management system assigns a priority to requests for desired surgical suite HVAC conditions from the surgical suite scheduling system.

6. The system of claim 1, wherein the facilities management system is a building management system.

7. The system of claim 6, wherein the building management system generates a report to one or both of a facility staff or a clinical staff in the event that a value of a parameter is outside of an acceptable range.

8. The system of claim 1, wherein the surgical suite comprises one or more surgical rooms, one or more patient rooms, and combinations thereof.

9. The system of claim 1, wherein the modes of operation for the surgical suite comprise at least a first surgery mode in which a surgery is scheduled for the surgical suite and a second setback mode in which no surgery is scheduled.

10. The system of claim 8, wherein the surgical suite comprises a patient room, and wherein the facilities management system controls the one or more heat exchangers, one or more dampers, and one or more blowers to provide desired HVAC settings based on whether a patient is checked-in.

11. The system of claim 8, wherein the surgical suite comprises a patient room, and wherein the facilities management system controls the one or more heat exchangers, one or more dampers, and one or more blowers to provide desired HVAC settings based on a scheduled appointment.

12. The system of claim 8, wherein the surgical suite comprises a patient room, and wherein the facilities management system controls the one or more heat exchangers, one or more dampers, and one or more blowers to provide desired HVAC settings based on a scheduled procedure.

\* \* \* \* \*